United States Patent [19]

Kusserow

[11] 4,133,046

[45] Jan. 2, 1979

[54] DEVICE FOR DISPLAYING A MEASURING VOLTAGE, FOR EXAMPLE AN EKG SIGNAL, ON THE VIEWING SCREEN OF AN OSCILLOGRAPH TUBE

[75] Inventor: Bernd Kusserow, Erlangen, Germany

[73] Assignee: Siemens Aktiengesellschaft, Berlin & Munich, Germany

[21] Appl. No.: 840,809

[22] Filed: Oct. 11, 1977

[30] Foreign Application Priority Data

Nov. 4, 1976 [DE] Fed. Rep. of Germany ....... 2650556

[51] Int. Cl.² .............................................. G11C 11/26
[52] U.S. Cl. ....................................... 365/45; 365/73; 365/118; 324/88
[58] Field of Search .......................... 365/45, 73, 118; 324/88 I

[56] References Cited

U.S. PATENT DOCUMENTS 3,652,999  3/1972  Hjort et al. ...................... 340/172.5

Primary Examiner—Terrell W. Fears
Attorney, Agent, or Firm—Hill, Gross, Simpson, Van Santen, Steadman, Chiara & Simpson

[57] ABSTRACT

In an illustrated embodiment an analog signal is sampled by means of a bucket brigade store. The stored samples are then repeatedly cycled through the store during refreshment of a visual display via a controlled amplifier. The storer also receives a reference voltage sample which is also circulated and which is periodically sampled at the storer output and compared with the input reference voltage, any deviation being utilized to control the amplification of the amplifier to maintain the reference voltage sample at substantially a constant level, and thus to maintain essentially unity amplification during the cyclical operation of the storer. The reference voltage sample can be selectively obtained from the measured signal or by means of a separate reference voltage generator. In the latter instance, the reference voltage sample is to be blocked so as to avoid display thereof, a previous sample of the measuring signal, for example, being displayed instead. For example, a scanner switch at the output of the bucket brigade storer may alternativey supply successive signal samples to the display and the reference voltage sample to a voltage comparator controlling amplification, a storage capacitor in the display circuit retaining the previous signal sample value during each amplifier calibration cycle.

12 Claims, 1 Drawing Figure

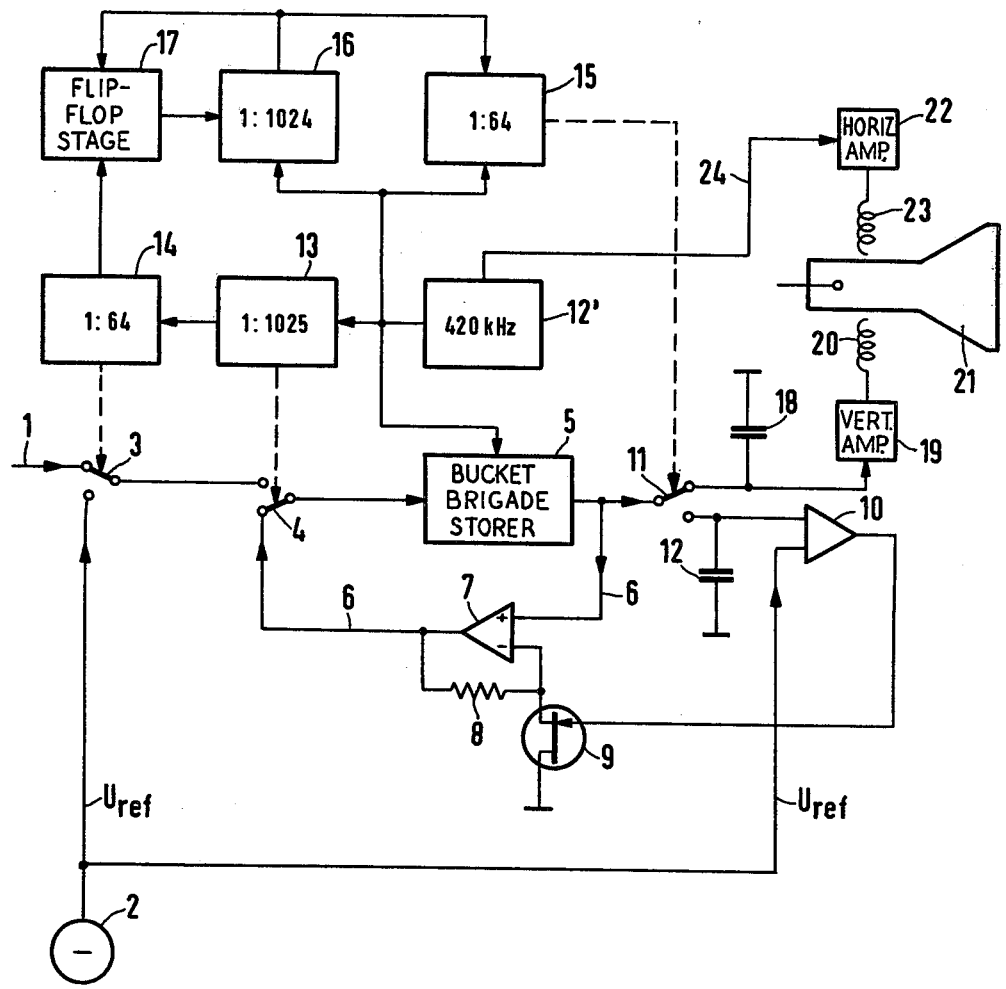

DEVICE FOR DISPLAYING A MEASURING VOLTAGE, FOR EXAMPLE AN EKG SIGNAL, ON THE VIEWING SCREEN OF AN OSCILLOGRAPH TUBE

BACKGROUND OF THE INVENTION

The invention relates to a device for displaying a measuring voltage, for example an EKG signal, on the viewing screen of an oscilloscope tube wherein values of the measuring voltage arriving in chronological succession are stored in an image repeating storer in corresponding chronological sequence and are read out in cyclic repetition from the latter onto the signal deflection system.

In known devices of this type (for example, U.S. Pat. No. 3,652,999), circulating shift registers for digital measured values of the measured quantity function as image repeating storers. For this purpose, the measuring voltage is digitized by means of analog-digital converters, whereby the digital measured values arriving in this fashion are cyclically read into the shift register and again cyclically read out from this shift register. In a digital-analog converter the measured values which have been read out, respectively, are reconverted into corresponding analog measured values which are finally conveyed to the signal deflection system of the oscilloscope tube for the purpose of image construction. The most recent devices of this type, in a practical embodiment, require seven to ten shift registers each with a 1024-bit storage capacity in order to achieve suitable delay times together with a desired resolution. However, the relatively high number of shift registers required, together with the associated analog-digital converters and digital-analog converters increases the cost of the overall construction of the device.

SUMMARY OF THE INVENTION

It is the object of the present invention to avoid this disadvantage of conventional devices.

In accordance with the invention, the object is achieved by virtue of the fact that a bucket brigade storer with signal feedback from output to input has an adjustable amplification in the feedback path and functions as the image repeating storer wherein the measured values of the measuring voltage are stored in an analog fashion, there being associated with the bucket brigade storer a reference voltage generator at the input side and a voltage comparator at the output side, the voltage comparator comparing the reference voltage value after having passed through the bucket brigade storer with a reference voltage value of a reference voltage means and, in the case of deviations between these values, adjusting the amplification degree of the bucket brigade storer such that the same reference voltage values occur at the input and at the output of the bucket brigade storer.

The invention utilizes a so-called bucket brigade storer such as is already known e.g. from "Philips Technische Rundschau", 31st year, 1970/71, No. 4, or from the "Bucket-Brigade Device" of the Reticon Corporation (an analog device using N-channel silicon-gate technology in a bucket-brigade configuration). A bucket brigade storer such as this which consists of a plurality of consecutive storage capacitors with intermediate switches for controlling further transmission of analog data, corresponds in its current market price approximately to that of a single shift register with the same number of storage places. In addition, the even more expensive analog-digital converters and digital-analog converters can be dispensed with. As a consequence, the overall cost outlay is substantially reduced. However, the use of a bucket brigade storer introduces the following problem: The amplification factor of the bucket brigade storer is not precisely unity; i.e., during circulation of the measuring signal, a small level decrease would cause the read-in information to approach zero. An amplification degree greater than one, on the contrary, leads to undesired oscillations of the circuit. However, the invention solves the problem by supplying the bucket brigade storer with a reference voltage value $U_{ref}$ contemporaneously with the measuring signal; for example an EKG signal. This reference voltage value circulates together with the analog measured values of the measuring voltage whereby, however, at the output of the bucket brigade storer the reference voltage is in each instance cyclically selected and compared with an originally stored reference voltage or with the output of a constant voltage source which supplies the reference voltage samples to the storer. The deviation is conveyed by the comparator in the form of a control voltage to a control amplifier which ensures that reference voltage values which are always of equal magnitude occur at the input and at the output of the bucket brigade storer. The latter instance is achieved when the amplification of the bucket brigade storer amounts precisely to unity. This signifies, in turn, that the amplitude characteristic of read-in information is maintained at a constant, as well as that the danger of the circuit beginning to oscillate is avoided.

In the device in accordance with the invention, in a preferred embodiment, the reference voltage value can be selectively obtained from the measured signal or by means of an external constant reference voltage generator. In the latter instance, $U_{ref}$ is to be eliminated from the signal to be displayed. In order that it not become visible in the displayed image. In the first instance, no blocking of the reference signal component is necessary, since $U_{ref}$ forms a component of the signal to be displayed. However, for the possible comparison of $U_{ref}$ at the output, with $U_{ref}$ at the input of the bucket brigade storer, an additional storer must be present in order to store the instantaneous value of the measuring voltage scanned at specific time intervals and utilized as the reference voltage $U_{ref}$. The necessary chronologically correct selection of the reference value at the output of the bucket brigade storer in the cadence of arrival of the high frequency storer cycle is also important. For the latter purpose, there is a sample-and-hold circuit with scanner switches, which, with a predeterminable stepping down of the cyclic shifter pulse frequency of the bucket brigade storer, connects the circulating reference signal sample to a storage capacitor of the sample-and-hold circuit. Through a corresponding synchronization of divider frequencies with the feeder pulse frequencies for the reference voltage values being fed into the bucket brigade storer, by means of additional input frequency dividers and also a flip-flop stage, it is possible for those storage values arriving precisely with the actuating pulses for the scan switch at the output of the bucket brigade storer to also be always precisely coordinated with previously stored and presently circulating reference voltage values. Thus reference voltage values which have just previously passed through the bucket brigade storer are always present at the storage capacitor of the sample-and-hold circuit and hence also at the actual value input of the voltage comparator. The pulse rate controlling new storages is coordinated with the arrival clock-pulse rate controlling sampling of the reference voltage values at the output of the bucket brigade storer.

Other objects, features and advantages of the invention will be apparent from the following detailed description taken in connection with the accompanying sheet of drawings.

BRIEF DESCRIPTION OF THE DRAWING

The single FIGURE of drawings shows a basic circuit diagram for controlling display of a measuring voltage on the viewing screen of an oscilloscope, in accordance with an illustrative embodiment of the invention.

DESCRIPTION OF THE PREFERRED EMBODIMENTS

In the FIGURE, which illustrates in a basic circuit diagram a sample embodiment of the invention, 1 denotes the input for a measuring voltage; i.e., in the present instance, for an EKG signal, and 2 denotes a reference voltage generator (constant D.C. voltage source) for supplying a constant reference voltage $U_{ref}$. The latter voltages, i.e., the measuring voltage as well as the reference voltage, are capable of being connected by means of switches 3 and 4 in preselectable time segments to the signal input of a so-called bucket brigade storer (storage capacitors with intermediate switches for controlling further transmission of analog data). The functional principle of this bucket brigade storer is that the voltage value information delivered at the input is shifted by means of clock pulses from storage capacitor to storage capacitor in the form of analog voltage values until, after a specified intermediate storage time which is dependent upon the number of storage locations as well as the shifter pulse frequency within the bucket brigade storer, the analog voltage values finally again emerge at the storer output. The bucket brigade storer 5, which preferably exhibits 1024 individual storage elements, functions as an image repeating storer. Accordingly, it comprises a feedback line 6 into which a signal amplifier 7 for the purpose of amplifying the feedback signal values is connected. The feedback output signal of the bucket brigade storer 5 is delivered via the feedback line 6 to the non-inverting input of the amplifier 7 constructed in the form of an operational amplifier. The inverting input has a feedback connection to the amplifier output via a feedback resistance 8. The field effect transistor 9, also connected to the inverting input of the operational amplifier 7, functions as a regulating element for adjustably varying the degree of amplification provided by amplifier 7. This adjustment proceeds by means of a resistance change at transistor 9 in dependence upon the output signal of the voltage comparator 10. The latter voltage comparator 10 serves the purpose of comparing the voltage reference value subsequent to passage through the bucket brigade storer 5 with that which was originally stored in storer 5 by scanning the $U_{ref}$ output of the reference voltage generator 2. Scanning of the reference value at the output of the bucket brigade storer 5 proceeds in the sample-and-hold technique by means of a scanner switch 11 in connection with a storage capacitor 12 at the actual value input of comparator 10. The nominal value input of comparator 10 is connected to the reference voltage $U_{ref}$ of reference voltage generator 2.

In order to predetermine the cyclic shifter pulse frequency of the bucket brigade storer 5, there is a central clock pulse generator 12' which operates for example with a clock pulse frequency of approximately 420 kHz. By means of frequency division of the shifter pulse frequency in the ratio of 1:1025 by means of a first frequency divider 13, the clock pulse frequency for switch 4 is obtained; i.e., the insertion pulse rate for controlling insertion of new analog information into the bucket brigade storer 5, and through a further division of this insertion clock pulse frequency in the ratio of 1:64 by means of a second frequency divider 14, the reference feed clock pulse rate for controlling the feeding of reference voltage values $U_{ref}$ via switch 3 into the bucket brigade storer 5 is finally obtained. Thus, due to the selected divider ratios, each 64th scan value (which is stored in the bucket brigade storer and which circulates in the latter) is a reference voltage $U_{ref}$. The intermediate values are, by contrast, analog values of the measuring voltage; i.e., of the EKG signal. For a chronologically correct selection of reference voltage values $U_{ref}$ at the output of the bucket brigade storer 5 — pursuant to a high frequency cyclic clock pulse rate for the analog data in the storer — by means of scanner switch 11 of the sample-and-hold circuit, a switch control installation is provided comprising a third as well as a fourth frequency divider. The third frequency divider 15 divides the cyclic shifter pulse frequency of the clock pulse generator 12' directly in the ratio of 1:64, whereas the fourth frequency divider 16 divides the clock pulse frequency in the ratio of 1:1024. The fourth frequency divider 16 is set at count-beginning (zero) by means of a flip-flop stage 17 when the second frequency divider 14 for the reference feed clock pulse produces a feed-in pulse for the reference voltage $U_{ref}$. At least upon receiving the first 1024th impulse of the cyclic shifter clock pulse frequency, the fourth frequency divider 16 then sets the third frequency divider 15 at count-beginning. In addition, the flip-flop stage 17 is also returned to the initial state by means of the fourth frequency divider 16 upon receiving the 1024th pulse, respectively. On the basis of the described control mechanism, it is thus possible that, after 1024 plus 64 voltage values at the output of the bucket brigade storer 5, the respective first reference voltage value is detected, and subsequently, in the 64-voltage-value rhythm, each additional arriving reference voltage value is detected, and connected to the storage capacitor 12 and thus to the actual value input of the comparator 10 by means of the scanner switch 11 actuated at this moment. The actual value of the voltage reference value which has thus arrived is now compared with the original reference value $U_{ref}$ by the comparator. If there are differences in these values, a control (or regulation) of the amplification degree of amplifier 7 results via transistor 9, in dependence upon the output signal of comparator 10. The control (or regulation) takes place until the output signal of the comparator 10 disappears; i.e., $U_{ref}$ at the input of the bucket brigade storer 5 and $U_{ref}$ at the output of the bucket brigade storer 5 are of equal magnitude.

Insofar as an external constant reference voltage generator 2 for the reference voltage value $U_{ref}$ is provided, as in the case of the present sample embodiment, the reference voltage value should be capable of being blocked out from the display for the measuring signal as soon as it appears at the output of the bucket brigade storer 5. Scanner switch 11 serves this purpose of blocking out the reference voltage value in the present instance, said switch interrupting the signal path to the display means in each instance during arrival of the reference voltage value. In the present case, the signal path comprises a storage capacitor 18 as well as a vertical amplifier 19 with the vertical deflection coil 20 of an oscillograph tube 21 as the display means. Storage capacitor 18 retains the previously arrived analog value of the measuring signal, respectively, during interruption of the signal path by the scanner switch 11. Thus blanking intervals in the signal display are avoided. The oscillograph tube 21, in a conventional fashion, additionally comprises a horizontal deflection amplifier 22 with the horizontal deflection coil 23. The horizontal deflection of the electron beam of the tube 21 proceeds via a control line 24 in the synchronous cadence of the clock-pulses of the clock pulse generator 12'.

It will be apparent that many modifications and variations may be effected without departing from the scope of the novel concepts and teachings of the present invention.

I claim as my invention:

1. A device for displaying a measuring voltage on a viewing screen wherein the values of the measuring voltage arriving in chronological succession are stored in corresponding chronological sequence, and are read out in cyclical repetition, characterized in that a bucket brigade storer (5), capable of signal feedback from output to input with adjustable amplification, functions as an image repeating storer with the measured values of the measuring voltage being stored in analog fashion, a reference voltage means (2) being associated with the bucket brigade storer at its input side for supplying a reference voltage value thereto, and a voltage comparator (10) at its output side, the voltage comparator (10) being operable to compare the reference voltage value after it has passed through the bucket brigade storer with a reference voltage value ($U_{ref}$) of the reference voltage means, and, in the case of deviation in the two values, being operable to adjust the amplification of the bucket brigade storer such that substantially equal reference voltage values occur at the input and output of the bucket brigade storer.

2. A device according to claim 1, characterized in that the reference value ($U_{ref}$) of the reference voltage means is obtained from the measuring signal.

3. A device according to claim 1, characterized in that the reference voltage value ($U_{ref}$) is briefly produced at predeterminable time intervals at the input to the bucket brigade storer (5).

4. A device according to claim 3, characterized in that the time intervals of new storage of reference voltage values ($U_{ref}$) are determined by a reference feed clock pulse rate which amounts to a fraction of the insertion clock pulse rate which controls insertion of new analog information into the bucket brigade storer (5).

5. A device according to claim 4, characterized in that in order to predetermine a reference feed clock pulse rate as a fraction of the insertion clock pulse rate for controlling insertion of new analog information into a bucket brigade storer (5) with a total of n storage locations, there are provided two frequency dividers (13, 14) connected in series, the first frequency divider (13) dividing the cyclic shifter clock pulse frequency of the bucket brigade storer, division of said shifter clock pulse frequency preferably being by a factor of n + 1 to produce the insertion clock pulse rate, and the second frequency divider (14), in turn, dividing this insertion clock pulse rate by a factor of m to produce the reference feed clock pulse rate.

6. A device according to claim 5, characterized in that, for a chronologically correct selection of the reference voltage values at the output of the bucket brigade storer (5) pursuant to a high frequency cyclic clock pulse rate of the analog data in the storer, a scanner switch (11) and a sample-and-hold circuit are connected to the output of the bucket brigade storer (5), and a switch control installation for the scanner switch (11) is provided comprising a third as well as a fourth frequency divider, whereby the third frequency divider (15) controls the scanner switch (11) and directly divides the cyclic shifter clock pulse rate in the ratio of 1:m, and the fourth frequency divider (16) divides the clock pulse frequency in the ratio of 1:n, the fourth frequency divider (16) being set at count-beginning when the second frequency divider (14) for the reference feed clock pulse produces a feed-in pulse for reference voltage ($U_{ref}$) and sets the third frequency divider (15) at count-beginning at least upon receiving the first nth pulse of the cyclic shifter clock pulse frequency.

7. A device according to claim 6, characterized in that a flip-flop stage (17) is connected to the fourth divider stage (16) for setting the fourth divider stage (16) to count-beginning, the fourth frequency divider (16), upon receiving the respective nth pulse, being operative to return the flip-flop stage (17) to an initial state.

8. A device according to claim 1, characterized in that, in order to adjust the amplification of the bucket brigade storer (5), a control amplifier (7) is provided in the storer feedback circuit (6), whose amplification is variable in dependence upon an output signal of the comparator (10) by means of a regulating element (9) such that the reference voltage values at the input and at the output of the bucket brigade storer are substantially equal.

9. A device according to claim 1, characterized in that, said reference voltage means comprising an external reference voltage generator (2), the reference voltage value being blocked out from the display of the measuring signal at the output of the bucket brigade storer (5).

10. A device according to claim 9, characterized in that, in conjunction with a display means (21) having a signal path for the measuring signal, in order to block out the reference voltage value, a scanner switch (11) is provided which, upon arrival of the reference voltage value, interrupts the signal path to the display means (21) in each instance.

11. A device according to claim 10, characterized in that an additional storage capacitor (18) is provided in the signal path to the display means (21) behind the scanner switch (11), which additional storage capacitor 18 retains the previously arrived analog value of the measuring signal when the signal path has been interrupted by the scanner switch (11).

12. A device according to claim 5, characterized in that, when a bucket brigade storer (5) is utilized having about n = 1024 storage locations, the first frequency divider (13) divides in the ratio of about 1:1025; the second (14) and third (15) frequency dividers divide in the ratio of about 1:64 (m = 64); and the fourth frequency divider (16) divides in the ratio of about 1:1024.

* * * * *